US012636472B2

(12) United States Patent
Gittard

(10) Patent No.: US 12,636,472 B2
(45) Date of Patent: May 26, 2026

(54) ENDOSCOPE STABILIZING CATHETER

(71) Applicant: C2Dx, Inc., Schoolcraft, MI (US)

(72) Inventor: Shaun Davis Gittard, Winston Salem, NC (US)

(73) Assignee: C2DX, INC., Schoolcraft, MI (US)

( * ) Notice: Subject to any disclaimer, the term of this patent is extended or adjusted under 35 U.S.C. 154(b) by 337 days.

(21) Appl. No.: 18/111,041

(22) Filed: Feb. 17, 2023

(65) Prior Publication Data

US 2023/0256214 A1 Aug. 17, 2023

Related U.S. Application Data

(60) Provisional application No. 63/311,287, filed on Feb. 17, 2022.

(51) Int. Cl.
*A61M 29/02* (2006.01)

(52) U.S. Cl.
CPC ....... *A61M 29/02* (2013.01); *A61M 2029/025* (2013.01); *A61M 2210/105* (2013.01)

(58) Field of Classification Search
CPC ............ A61M 29/02; A61M 2029/025; A61M 2210/105; A61M 2025/0177; A61M 2025/1081; A61M 25/04; A61B 1/0014; A61B 1/233
See application file for complete search history.

(56) References Cited

U.S. PATENT DOCUMENTS 5,372,055 A * 12/1994 Kelly .................. B25B 13/5016
81/53.2
5,904,648 A 5/1999 Arndt et al.
5,911,725 A * 6/1999 Boury .............. A61B 17/22031
606/108

(Continued)

FOREIGN PATENT DOCUMENTS

WO 2009070970 A1 6/2009

OTHER PUBLICATIONS

Arndt Endobronchial Blocker Sets, Cook Medical brochure, 2014, pp. 1-4.

(Continued)

*Primary Examiner* — Andrew Restaino
(74) *Attorney, Agent, or Firm* — Honigman LLP; Douglas H. Siegel

(57) ABSTRACT

An example catheter has an elongate member defining an elongate member proximal end, an elongate member distal end, an outer surface, and a main body, the outer surface defining a side opening at a position between the elongate member proximal end and the elongate member distal end, the main body defining a first lumen and a second lumen, the second lumen extending from the elongate member proximal end to the side opening; a balloon disposed on the elongate member between the side opening and the elongate member distal end; and an engagement member disposed in the second lumen, the engagement member defining an engagement member proximal end and an engagement member distal end, the engagement member proximal end extending axially beyond the elongate member proximal end, the engagement member distal end having an engagement portion and extending radially beyond the side opening in a first direction.

8 Claims, 7 Drawing Sheets

(56)  References Cited

U.S. PATENT DOCUMENTS

| | | | | |
|---|---|---|---|---|
| 6,071,233 A * | 6/2000 | Ishikawa | .............. | A61B 1/0014 |
| | | | | 600/129 |
| 7,578,295 B2 | 8/2009 | Kurrus | | |
| 9,889,265 B2 | 2/2018 | Fischer, Jr. et al. | | |
| 10,065,028 B2 | 9/2018 | Liberatore et al. | | |
| 2002/0077651 A1* | 6/2002 | Holmes, Jr. | ........... | A61M 29/02 |
| | | | | 606/190 |
| 2008/0015540 A1* | 1/2008 | Muni | ................. | A61B 17/3421 |
| | | | | 604/502 |
| 2009/0030274 A1 | 1/2009 | Goldfarb et al. | | |
| 2011/0105840 A1 | 5/2011 | Terliue et al. | | |
| 2012/0029526 A1* | 2/2012 | Hewitt | ............. | A61B 17/00234 |
| | | | | 606/113 |
| 2012/0078235 A1* | 3/2012 | Martin | .............. | A61M 25/0017 |
| | | | | 604/544 |
| 2013/0096378 A1 | 4/2013 | Alexander et al. | | |
| 2021/0315448 A1 | 10/2021 | Makower et al. | | |

OTHER PUBLICATIONS

Hercules 100 Transnasal Esophageal Balloon, Cook Medical brochure, 2020, pp. 1-8.
Hercules 100 Transnasal Esophageal Balloon, Cook Medical, retrieved Oct. 29, 2021, URL https://www.cookmedical.com/products/2691eb8a-dc2f-4236-84e6-56212d1d8fc7/.

* cited by examiner

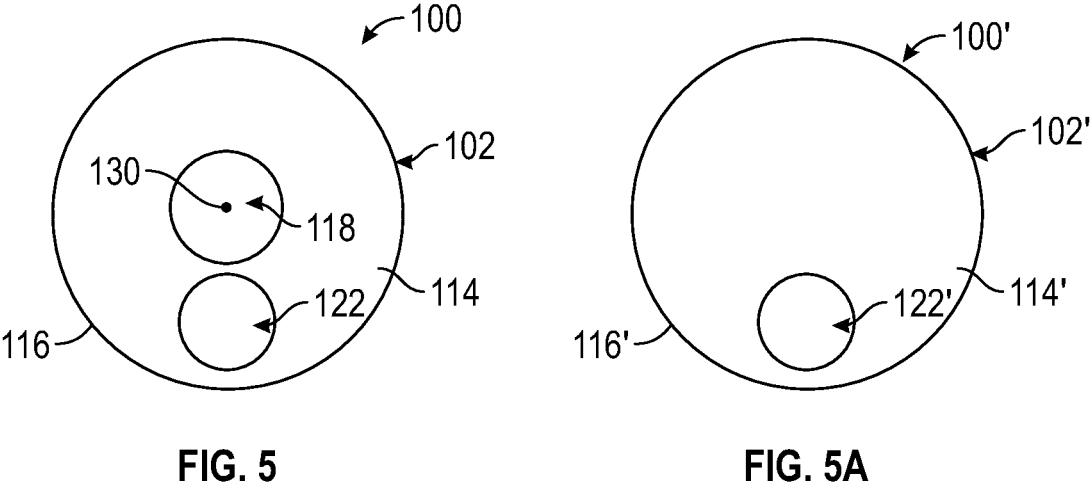
FIG. 5             FIG. 5A
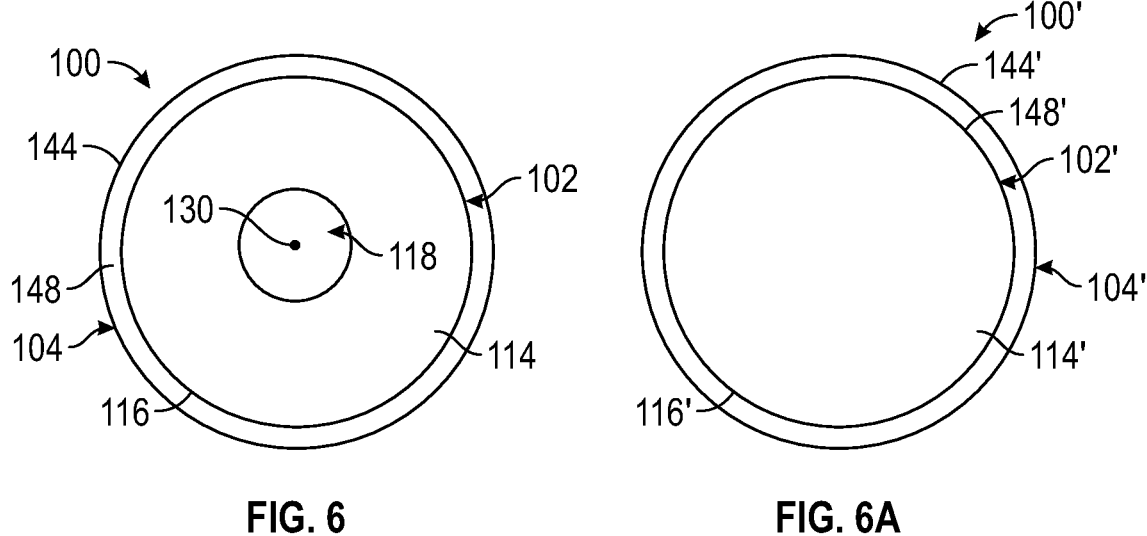
FIG. 6             FIG. 6A

ENDOSCOPE STABILIZING CATHETER

FIELD

The disclosure relates to medical devices. More particularly, the disclosure relates to catheters, catheter systems, and methods of treatment. Specific examples described herein relate to balloon catheters useful in transnasal esophageal dilation.

BACKGROUND

Many medical procedures require a catheter and a secondary instrument, such as an endoscope, to be inserted into a body of a patient. For example, in transnasal esophageal dilation procedures, a balloon catheter is advanced through one nostril, while the endoscope is advanced either through the same nostril or the other nostril until the endoscope is alongside the balloon catheter. This transnasal approach and side-by-side arrangement of instruments allows a practitioner to perform esophageal dilation in an office setting, without requiring administration of anesthesia to the patient.

However, the side-by-side configuration of the balloon catheter and the endoscope can present challenges in these procedures. For example, maintaining alignment of the endoscope and the balloon catheter can be difficult, which may impact visualization of the balloon and the surrounding tissue.

While the art includes examples of devices for stabilizing secondary instruments against catheters, these devices are not suitable for use in procedures that require visualization of a balloon in its inflated configuration.

A need exists, therefore, for improved catheters, catheter systems, and methods of treatment.

BRIEF SUMMARY OF SELECTED EXAMPLES

Various example catheters are described.

An example catheter comprises an elongate member defining an elongate member proximal end, an elongate member distal end, an outer surface, and a main body, the outer surface defining a side opening at a position between the elongate member proximal end and the elongate member distal end, the main body defining a first lumen and a second lumen, the first lumen extending from the elongate member proximal end to the side opening, the second lumen extending from the elongate member proximal end toward the elongate member distal end; a balloon disposed on the elongate member between the side opening and the elongate member distal end, the balloon having a balloon wall that defines a balloon cavity in fluid communication with the third lumen; and an engagement member disposed in the second lumen, the engagement member defining an engagement member proximal end and an engagement member distal end, the engagement member proximal end extending axially beyond the elongate member proximal end, the engagement member distal end extending radially beyond the side opening in a first direction, and the engagement member distal end having an engagement portion.

Another example catheter comprises an elongate member defining an elongate member proximal end, an elongate member distal end, an outer surface, and a main body, the outer surface defining a side opening at a position between the elongate member proximal end and the elongate member distal end, the main body defining a first lumen, a second lumen, and a third lumen, the first lumen extending from the elongate member proximal end to the elongate member distal end, the second lumen extending from the elongate member proximal end to the side opening, the third lumen extending from the elongate member proximal end toward the elongate member distal end; a balloon disposed on the elongate member between the side opening and the elongate member distal end, the balloon having a balloon wall that defines a balloon cavity in fluid communication with the third lumen; an engagement member disposed in the second lumen, the engagement member defining an engagement member proximal end and an engagement member distal end, the engagement member proximal end extending axially beyond the elongate member proximal end, the engagement member distal end extending radially beyond the side opening toward the elongate member proximal end and biased in a first direction, the engagement member distal end having an engagement portion; and a retractable catheter sheath disposed over the elongate member, the balloon, and the engagement distal end, and having an inner surface contacting the engagement portion.

Various example catheter systems are described.

An example catheter system includes a catheter according to any embodiment and can include any suitable secondary instrument. Also, a catheter system can include a secondary instrument joined with the engagement member of the catheter, or the secondary instrument can be free of the engagement member and configured to be joined with the engagement member by a user of the catheter system.

Various example methods of treatment are described.

An example method of treatment includes advancing a catheter according to an embodiment into a body vessel of a patient; advancing a secondary instrument through a body vessel to the engagement portion of the catheter; joining the secondary instrument with the engagement portion to engage the secondary instrument with the engaging member; retracting the engagement member within the second lumen of the catheter to move the engagement portion toward the side opening of the elongate member and to move the secondary instrument toward the side opening of the elongate member; performing a treatment within the body vessel using the catheter; retracting the secondary instrument through the body vessel to disengage the secondary instrument from the engagement member; and retracting the catheter through the body vessel.

An example method of performing transnasal esophageal dilation includes advancing a catheter according to an embodiment through a nostril and into the esophagus of a patient; advancing the engagement member of the catheter within the second lumen of the elongate member to extend the engagement portion of the engagement member radially beyond the side opening of the elongate member; advancing an endoscope through a nostril and into the esophagus of the patient to the engagement portion of the engagement member; joining the distal end of the endoscope with the engagement portion of the engagement member to engage the endoscope with the engagement member; retracting the engagement member within the second lumen of the elongate member to move the engagement portion toward the side opening of the elongate member and to move the endoscope toward the side opening of the elongate member; inflating the balloon to dilate tissue of the esophagus surrounding the balloon; visualizing the balloon using the endoscope while the endoscope is engaged with the engagement member; deflating the balloon of the catheter; retracting the endoscope through the nostril to disengage the endoscope from the engagement member; and retracting the catheter through the nostril.

Additional understanding of the inventive catheters, catheter systems, and methods of treatment can be obtained by reviewing the detailed description of selected examples, below, and the referenced drawings.

DESCRIPTION OF FIGURES

FIG. 5 is a sectional view of the example catheter illustrated in FIG. 3 taken along section line B-B in FIG. 3.

FIG. 5A is another sectional view of the alternative catheter illustrated in FIG. 4A, taken at the same location in the alternative catheter as the section illustrated in FIG. 5 is taken in the example catheter illustrated in FIG. 3.

FIG. 6 is a sectional view of the example catheter illustrated in FIG. 3 taken along section line C-C in FIG. 3.

FIG. 6A is another sectional view of the alternative catheter illustrated in FIG. 4A, taken at the same location in the alternative catheter as the section illustrated in FIG. 6 is taken in the example catheter illustrated in FIG. 3.

DETAILED DESCRIPTION OF SELECTED EXAMPLES

Figure 1:
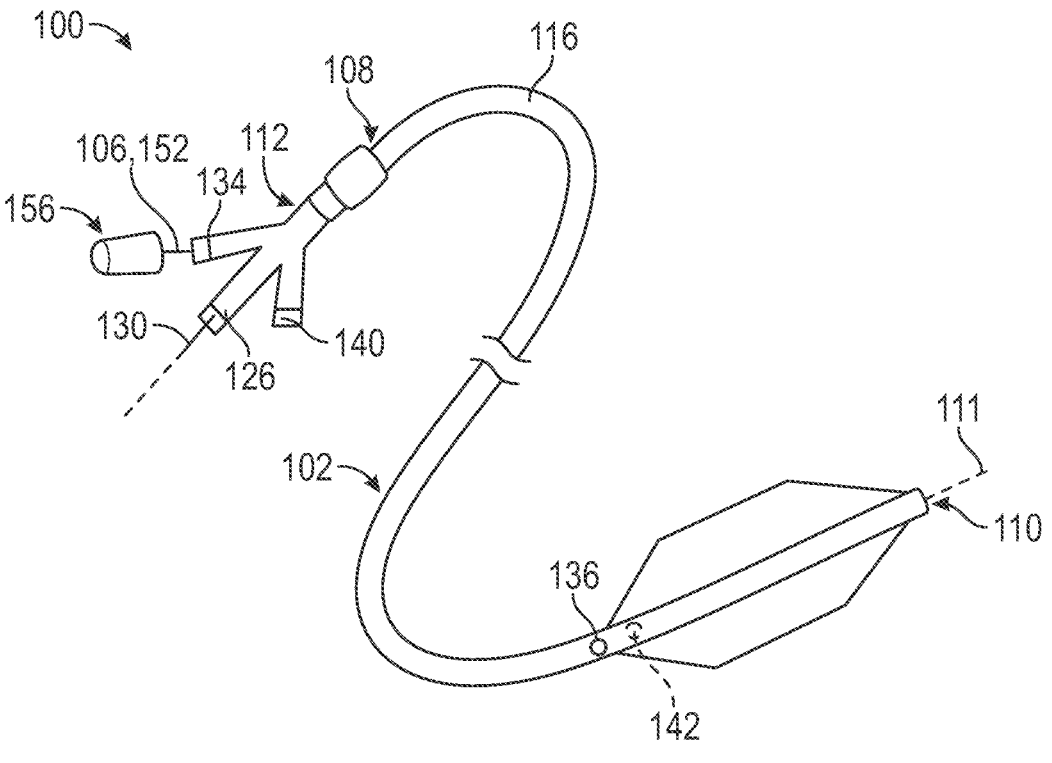
FIG. 1 is a top plan view of an example catheter, partially broken away.

The following detailed description and the appended drawings describe and illustrate various example catheters, catheter systems, and methods of treatment. The description and illustration of these examples enable one skilled in the art to make and use examples of the inventive catheters and catheter systems, and to practice examples of the inventive methods of treatment. They do not limit the scope of the claims in any manner.

Each of FIGS. 1, 2, 3, 4, 5, and 6, illustrates a first example catheter 100. The catheter 100 has an elongate member 102, a balloon 104, and an engagement member 106. The elongate member 102 is a substantially tubular member. The elongate member 102 defines an elongate member proximal end 108 and an elongate member distal end 110. The elongate member proximal end 108 is defined opposite to the elongate member distal end 110 relative to a lengthwise axis 111 of the elongate member 102. The elongate member proximal end 108 is connected to a catheter handle 112. The catheter handle 112 is a substantially rigid member, which can be used to manipulate the catheter 100. The elongate member 102 defines a main body 114 and an outer surface 116. The main body 114 defines a first lumen 118, a second lumen 120, and a third lumen 122.

Figure 2:
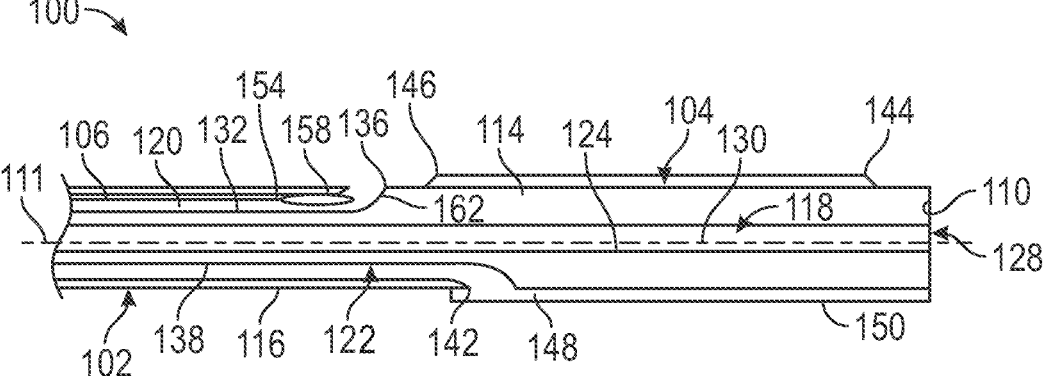
FIG. 2 is a side view of the distal end portion of the example catheter illustrated in FIG. 1. The balloon of the catheter is illustrated in an unexpanded configuration.
Figure 3:
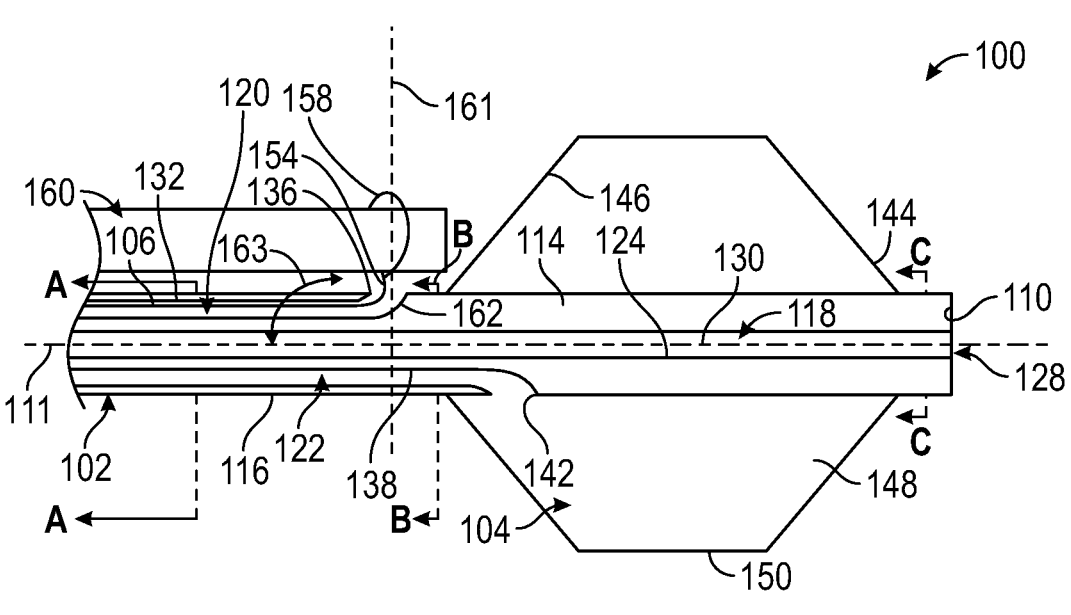
FIG. 3 is a side view of the distal end portion of the example catheter illustrated in FIG. 1 in an example catheter system. The balloon of the catheter is illustrated in an expanded configuration. A secondary instrument is disposed alongside the catheter and engaged with an engagement member of the catheter.

The first lumen 118 extends through the elongate member 102 from the elongate member proximal end 108 to the elongate member distal end 110. The main body 114 of the elongate member 102 defines a first lumen inner surface 124 and a first lumen distal opening 128 that forms a distal, terminal opening of the first lumen 118 on the elongate member distal end 110. The first lumen 118 extends to and is in communication with the first lumen distal opening 128. The catheter handle 112 defines a first handle lumen 126. The first handle lumen 126 extends to and is in communication with the first lumen 118. As best illustrated in FIGS. 2 and 3, the first handle lumen 126 and the first lumen 118 can receive a guidewire 130, which can extend through the first lumen distal opening 128, out of the first lumen 118, and away from the catheter 100. This structural configuration allows catheter 100 to be disposed over and advanced along a guidewire, such as a guidewire that has been previously placed within a body vessel, using conventional over-the-wire navigation and placement techniques.

The main body 114 of the elongate member 102 defines a second lumen inner surface 132. The catheter handle 112 defines a second handle lumen 134 that extends to and is in communication with the second lumen 120. The outer surface 116 of the elongate member 102 defines a side opening 136 that forms a distal, terminal opening of the second lumen 120. The second lumen 120 extends to and is in communication with the side opening 136. Specifically, the second lumen 120 extends through the elongate member 102 from the elongate member proximal end 108 to the side opening 136. The side opening 136 provides communication between the second lumen 120 and an environment outside of the catheter 100, e.g., the body of the patient.

The axial position of the side opening 136 on the elongate member 102 is important to the invention. As best illustrated in FIG. 1, the side opening 136 is disposed on the outer surface 116 of the elongate member at a position that is axially between the elongate member proximal end 108 and the balloon 104 with respect to the lengthwise axis 111 of catheter 100. Also as best illustrated in FIG. 1, the side opening 136 is disposed substantially closer to the balloon 104 than the elongate member proximal end 108 with respect to lengthwise axis 111 of catheter 100. A skilled artisan will be able to select a suitable position of the side opening relative to the balloon in a catheter according to a particular embodiment based on various considerations, including any desired positioning of these elements within a body lumen during an intended use of the catheter. For example, the inventor has determined that, for a catheter intended for use in a method of performing transnasal esophageal dilation, such as method 500 described in detail below and illustrated in FIG. 11, a position that places the side opening less than or equal to about 10 cm from the proximal side of the balloon is considered suitable at least because this relative positioning between the side opening and the proximal side of the balloon is expected to position the engagement between the engagement portion 158 of the engagement member 106 and a secondary instrument 160 within the oral cavity, which is desirable for these procedures. Also for a catheter intended for use in a method of performing transnasal esophageal dilation, a position that places the side opening less than or equal to about 5 cm from the proximal side of the balloon is considered suitable for at least the same reason. Also for a catheter intended for use in a method of performing transnasal esophageal dilation, a position that places the side opening less than or equal to about 3 cm from the proximal side of the balloon is considered suitable for at least the same reason. Also for a catheter intended for use in a method of performing transnasal esophageal dilation, a position that places the side opening between about 1 cm and about 3 cm from the proximal side of the balloon is considered suitable for at least the same reason.

The third lumen 122 extends through the elongate member 102 from the elongate member proximal end 108, toward the elongate member distal end 110, and to the balloon 104. The main body 114 of the elongate member 102 defines a third lumen inner surface 138 and a third lumen distal opening 142. The third lumen distal opening 142 forms a distal, terminal opening of the third lumen 122 and is disposed on the outer surface 116 of the elongate member at a position that is axially within the axial length of the balloon 104 with respect to the lengthwise axis 111 of catheter 100. The third lumen distal opening 142 provides fluid communication between the third lumen 122 and the balloon 104, allowing advancement and withdrawal of a fluid through the third lumen 122 to inflate and deflate the balloon 104 in convention manner. The catheter handle 112 defines a third handle lumen 140. The third handle lumen 140 can be connected to a fluid-filled syringe or other fluid supply to enable inflation and deflation of the balloon.

The balloon 104 is disposed on the outer surface 116 of the elongate member 102 between the elongate member proximal end 108 and the elongate member distal end 110. The balloon 104 is disposed around the outer surface 116 of the elongate member 102 at an axial position that is between the side opening 136 and the elongate member distal end 110 with respect to the lengthwise axis 111 of catheter 100. The balloon 104 defines a balloon distal portion 144 and a balloon proximal portion 146. The balloon distal portion 144 is disposed between the balloon proximal portion 146 and the elongate member distal end 110. The balloon proximal portion 146 is disposed between the side opening 136 and the balloon distal portion 144. The balloon 104 has a balloon wall 150 that defines balloon cavity 148. Balloon cavity 148 is in fluid communication with the third lumen distal opening 142. As fluid is introduced into balloon cavity 148, balloon 104 inflates to an expanded configuration, illustrated in FIG. 3. This permits the balloon 104 to dilate a narrow opening or passage within the body of a patient. For example, during an esophageal dilation, the balloon 104 can be used to dilate a lumen of the esophagus. As fluid is withdrawn from balloon cavity 148, balloon 104 deflates to an unexpanded configuration, illustrated in FIG. 2.

The engagement member 106 is disposed in and axially movable within the second lumen 120. The engagement member 106 defines an engagement member proximal end 152 and an engagement member distal end 154. The engagement member proximal end 152 extends out of the second handle lumen 134, as illustrated in FIG. 1. The engagement member proximal end 152 can include an actuator, such as an engagement handle 156. The engagement handle 156 can be used to move the engagement member 106 axially within the second lumen 120. Other alternative actuators can also be employed. For example, a handle that includes one or more sliders, one or more buttons, another actuator, or any combination of these can be used. Movement of the engagement member 106 within the second lumen 120 moves the engagement member distal end 154 between a retracted position, illustrated in FIG. 2, and an extended position, illustrated in FIG. 3. In the extended position, the engagement member distal end 154 is extended at least partially out of the side opening 136, as illustrated in FIG. 3. In the retracted position, the engagement member distal end 154 is retracted at least partially through the side opening 136 and into the second lumen 120, as illustrated in FIG. 2. In some instances, the engagement member distal end 154 is completely retracted through the side opening 136 and into the second lumen 120. Desirably, the complete retraction of the engagement member distal end 154 minimizes the profile of the elongate member 102 for advancing or removing the elongate member 102 through the body of the patient. It should be appreciated that additional engagement members 106 can be employed, if desired. In some embodiments, the engagement member proximal end 152 is configured to releasably secure the engagement member 106 into a desired position, such as a desired extension distance of the engagement member distal end 154 out of the side opening 136. For example, the engagement member proximal end 152 can be configured to releasably lock tension of the engagement portion 158 of the engagement member distal end 154 around an engaged secondary instrument 160.

The engagement member distal end 154 has an engagement portion 158. The engagement portion 158 is used to join a secondary instrument 160, for example, an endoscope, to the engagement portion 158, when the engagement member distal end 154 is in the extended position, as illustrated in FIG. 3. After the engagement portion 158 is joined to the secondary instrument 160, the engagement member distal end 154 can be retracted toward the side opening 136, which pulls the secondary instrument 160 toward the side opening 136, enhancing the engagement between the elongate member 102 and the secondary instrument 160. Advantageously, this permits a practitioner to reposition the secondary instrument 160 into a side-by-side configuration with the elongate member 102. The axial position of the side opening 136 between the elongate member proximal end 108 and the balloon proximal portion 146 facilitates the alignment of the secondary instrument 160 into a side-by-side configuration, while also militating against the secondary instrument 160 from slipping out of alignment by sliding off the balloon 104. In certain examples, the engagement member distal end 154 is joined to an end portion of the secondary instrument 160.

While the engagement portion 158 in the illustrated example catheter 100 defines a loop, the engagement portion in a catheter according to a particular embodiment can have any suitable structure and a skilled artisan will be able to select a suitable structure based on various considerations, including the size and configuration of any secondary instrument with which the catheter is intended to be used. Non-limiting examples of structures considered suitable for the engagement portion in a catheter according to an embodiment include, but are not limited to, loops, fasteners, deposits of adhesive, suction cups, magnets, and other structures suitable for forming a structural engagement between two members. Other technologies and methods for selectively joining the engagement portion 158 to the secondary instrument 160 can also be employed.

In the example catheter illustrated in FIGS. 1 through 5, the engagement portion 158 is a loop 158. In operation, the loop 158 is moved into a position adjacent to the side opening 136 and the balloon 104 by moving the engagement member distal end 154 into the extended position. The secondary instrument 160 is advanced at least partially through the loop 158, as illustrated in FIG. 3. Once the secondary instrument 160 is at least partially disposed through the loop 158, the engagement member distal end 154 is moved into the retracted position, which causes the loop 158 to form a tight fit around the secondary instrument 160 and pull the secondary instrument 160 toward the side opening 136. Thus, the engagement portion 158 can be employed by a practitioner to maintain the secondary instrument 160 in close proximity to the balloon proximal portion 146. This can be particularly advantageous for medical procedures when the practitioner is interested in maintaining the secondary instrument 160 in close proximity to the balloon proximal portion 146. For example, a practitioner may want to maintain an endoscope near the proximal portion of the balloon 104 in order to visualize the balloon 104 and surrounding tissue during a dilation procedure.

In the example catheter 100 illustrated in FIGS. 1 through 5, the engagement member distal end 154 can be extended and retracted through the side opening 136 in a first direction. The first direction can be adjusted to facilitate axial stability of the secondary instrument 160 to the elongate member 102 when the engagement portion 158 pulls the instrument toward the side opening 136. The first direction can be along a first directional axis 161. A first direction angle 163 is defined by the first directional axis 161 and the longitudinal axis 111. The first direction angle 163 is oblique. In certain examples, the first direction angle 163 is substantially perpendicular the longitudinal axis 111. Non-limiting examples of predefined ranges for the first direction angle 163 include 45° to 90°, 60° to 90°, and 75° to 90°. However, it should be appreciated that a person skilled in the art can select a suitable angle for the first direction angle 163 in a catheter according to a particular embodiment based on various considerations, such as the structure and flexibility of the engagement member.

The engagement member distal end 154 can be extended and/or retracted through the side opening 136 of the elongate member 102 in the first direction using a variety of technologies and methods. In a non-limiting example, a portion of the second lumen inner surface 132 defines a slope 162 proximal to the side opening 136. The slope 162 can be a linear or curvilinear surface and advantageously has a slope angle that facilitates movement of the engagement member distal end 154 out of the side opening 136 in the first direction as the engagement member 106 is advanced axially within the second lumen 120. In the example catheter 100 illustrated in FIGS. 1 through 5, the slope angle is oblique to the longitudinal axis 111. In certain examples, the slope angle is acute. Non-limiting examples of predefined ranges for the slope angle include 0° to 90°, 15 to 90°, and 30° to 90°. However, it should be appreciated that a person skilled in the art can select a suitable slope angle for in a catheter according to a particular embodiment based on various considerations, such as the structure and flexibility of the engagement member.

In another non-limiting example, the engagement member distal end 154 is biased in the first direction so that the engagement member distal end 154 moves to the first direction when extended or retracted through the side opening 136. This can be accomplished by forming a predefined bend at the engagement member distal end 154. This may also be accomplished by manufacturing the engagement member distal end 154 from viscoelastic and/or elastic materials. These materials enable the engagement member distal end 154 to return to its original shape (the first direction) after the engagement member distal end 154 exits the side opening 136. Other technologies and methods for extending and/or retracting the engagement member distal end 154 in the first direction can be employed, as desired.

The catheter 100 may be manufactured from a variety of different materials, including conventional materials for minimally-invasive interventional medical devices such as catheters. Non-limiting examples of materials include vinyl, also known as polyvinyl chloride (PVC), rubber, latex, silicone, siliconized latex, and silicone elastomers. However, it should be appreciated that one skilled in the art can select alterative materials appropriate for medical devices, within the scope of this disclosure. The outer surface 116 of the elongate member 102 may have coatings to alter outer surface properties. For example, the outer surface 116 can be coated with polytetrafluoroethylene (PTFE) to reduce friction. Other non-limiting examples of coatings include hydrogels, silicone, silver, polyzwitterions, poly(ethylene glycol) (PEG), and hydrophilic polymers. Other coatings may also be employed, as desired. The balloon 104 can be manufactured from a variety of different materials. Non-limiting examples of materials include polyester, nylon, polyether block amide (PEBA) polyurethane, and silicone. However, it should be appreciated that one skilled in the art can select alterative materials appropriate for medical balloons 104, as desired.

The catheter 100 can have any suitable length. A skilled artisan can select a suitable length for a catheter according to a particular embodiment based on various considerations, such as an intended use of the catheter 100 or the expected dimensions of a body vessel within which the catheter is intended to be used. For example, the inventor has determined that, for a catheter intended for use in a method of performing transnasal esophageal dilation, such as method 500 described in detail below and illustrated in FIG. 11, a length of greater than about 30 cm is suitable at least because this catheter length provides sufficient length for a user to manipulate the catheter during a procedure while not requiring the user to be within a distance from the patient during such manipulation that may otherwise limit the ability to manipulate the catheter. Also for a catheter intended for use in a method of performing transnasal esophageal dilation, a length of between about 30 cm and about 90 cm is considered suitable for at least the same reason. Also for a catheter intended for use in a method of performing transnasal esophageal dilation, a length of greater than or equal to about 90 cm is considered suitable for at least the same reason.

Figures 4, 4A:
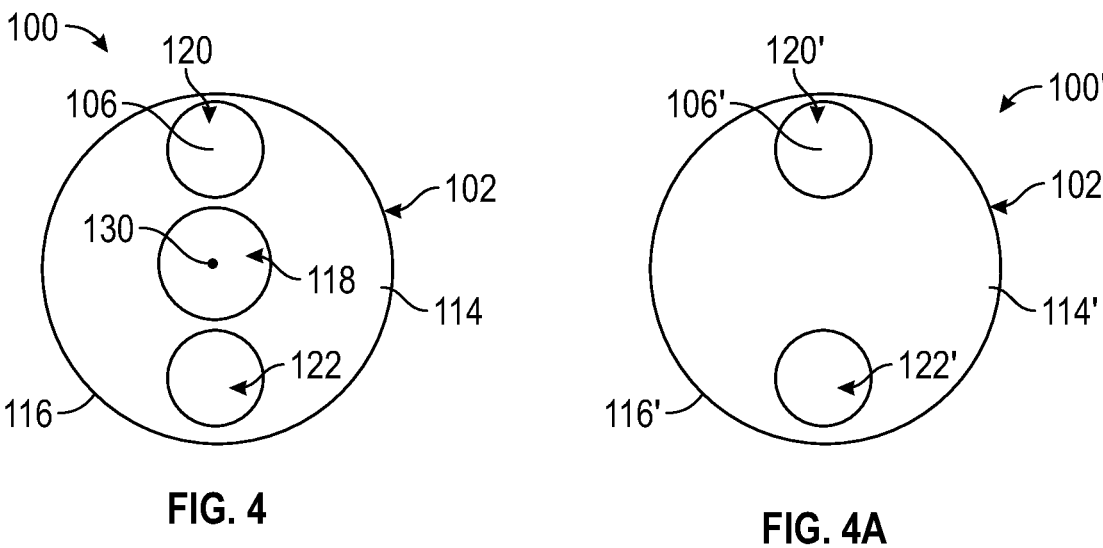
FIG. 4 is a sectional view of the example catheter illustrated in FIG. 3 taken along section line A-A in FIG. 3.
FIG. 4A is a sectional view of an alternative catheter, taken at the same location in the alternative catheter as the section illustrated in FIG. 4 is taken in the example catheter illustrated in FIG. 3.

Each of FIGS. 4A, 5A, and 6A illustrates a sectional view of an alternative catheter 100'. The alternative catheter 100' is similar to catheter 100 described above and illustrated in FIGS. 1, 2, 3, 4, 5, and 6, except as detailed below. In FIGS. 4A, 5A, and 6A, elements in catheter 100' referenced by a number with a prime mark correspond to the element in catheter 100 referenced by the same number without the prime mark. Thus, catheter 100' has an elongate member 102' that defines a main body 114' and an outer surface 116'. The main body 114' defines first 120' and second 122' lumens.

In this alternative embodiment, the main body 114' only defines two lumens 120', 122'. The central lumen 118 of catheter 100 is not present in catheter 100'. This structural arrangement can be advantageous for catheters intended for balloon dilation in the absence of a guidewire, for example.

Figure 7:
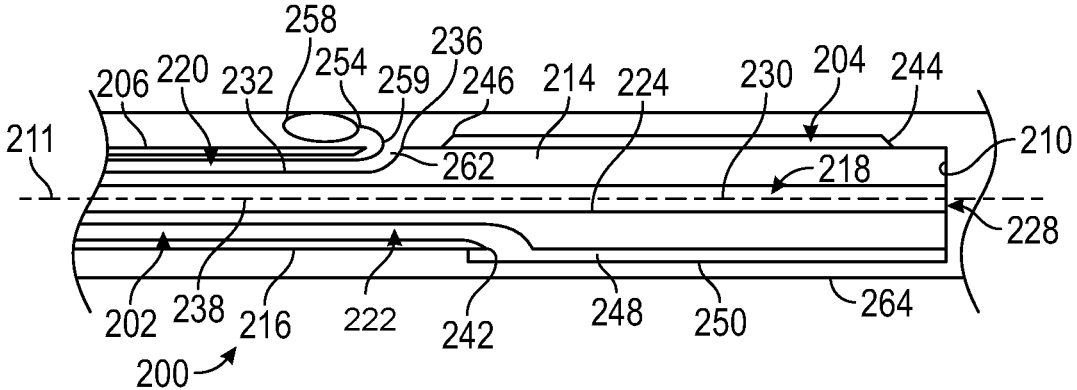
FIG. 7 is a side view of the distal end portion of another example catheter disposed within a sheath. The balloon of the catheter is illustrated in an unexpanded configuration.
Figure 8:
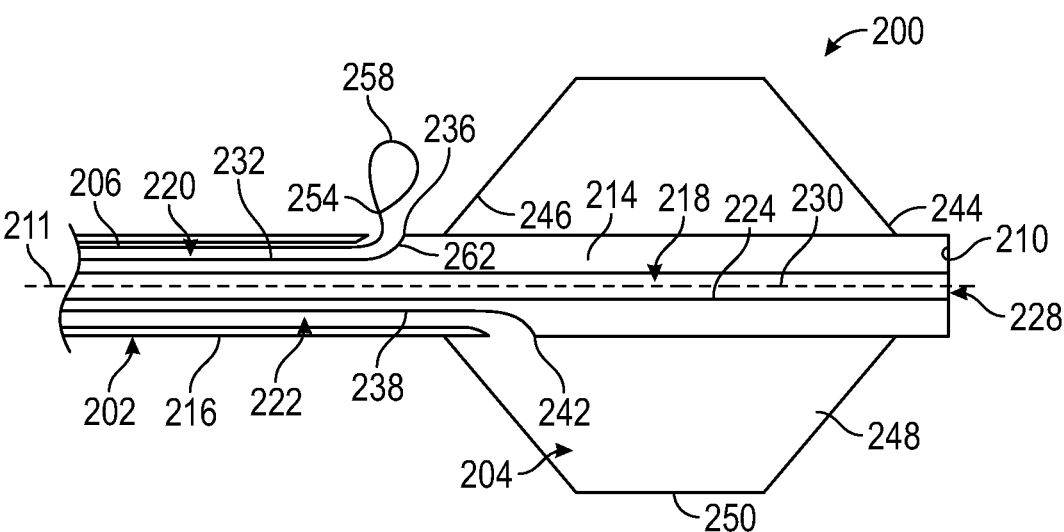
FIG. 8 is a side view of the distal end portion of the example catheter illustrated in FIG. 7. The balloon of the catheter is illustrated in an expanded configuration.

FIGS. 7 and 8 illustrate another example catheter 200. The catheter 200 is similar to the catheter 100, except as described below. Thus, the catheter 200 has an elongate member 202, a balloon 204, and an engagement member 206. The elongate member 202 defines an elongate member proximal end 208 and an elongate member distal end 210. The elongate member 102 defines a main body 214 and an outer surface 216. The main body 214 defines a first lumen 218, a second lumen 220, and a third lumen 222. The main body 214 of the elongate member 202 defines a first lumen inner surface 224 and a first lumen distal opening 228. The first lumen distal opening 228 is defined on the elongate member distal end 110. The first handle lumen 226 extends to and is in communication with the first lumen 218. The main body 214 of the elongate member 202 defines a second lumen inner surface 232. The outer surface 216 of the elongate member 202 defines a side opening 236 at an axial position between the elongate member proximal end 208 and the balloon 204 with respect to a longitudinal axis 211 of the catheter 200. The second lumen 220 extends to and is in communication with the side opening 236. The main body 214 of the elongate member 202 defines a third lumen inner surface 238 and a third lumen distal opening 242. The third lumen distal opening 242 is axially positioned within the axial length of the balloon 204 with respect to a longitudinal axis 211 of the catheter 200. The balloon 204 is disposed on the outer surface 216 of the elongate member 202 between the elongate member proximal end 208 and the elongate member distal end 210. The balloon 204 defines a balloon distal portion 244 and a balloon proximal portion 246. The balloon distal portion 244 is disposed between the balloon proximal portion 246 and the elongate member distal end 210. The balloon proximal portion 246 is disposed between the side opening 236 and the balloon distal portion 244. The balloon 204 has a balloon wall 250 that defines a balloon cavity 248. The engagement member 206 is disposed in and axially movable within the second lumen 220. The engagement member 206 defines an engagement member proximal end 252 and an engagement member distal end 254. The engagement member distal end 254 has an engagement portion 258. The catheter 100 can further include a retractable catheter sheath 264 disposed over the elongate member 202, the balloon 204, and the engagement member distal end 254.

In this embodiment, the engagement member distal end 254 may not fully retract into the second lumen 220. For example, during the initial insertion of the elongate member 202 into the body of the patient, the engagement member distal end 254 extends out of the side opening 236 and is oriented toward the elongate member proximal end 208, along with being biased in the first direction. The engagement portion 258 abuts the retractable catheter sheath 264, as the retractable catheter sheath 264 is disposed over the engagement member distal end 254, as illustrated in FIG. 7. Once the elongate member 202 is in a desired location in the body of the patient, the retractable catheter sheath 264 is at least partially withdrawn toward the elongate member proximal end 208. When the catheter retractable sheath 264 is at least partially withdrawn, the engagement member distal end 254 moves to the first direction, as illustrated in FIG. 5. Once this occurs, a secondary instrument 160 can be advanced to the engagement portion 258 to be joined to the engagement portion 258. For example, in circumstances where the engagement portion 258 is a loop 258. The secondary instrument 160 is advanced at least partially through the loop 258.

The engagement member distal end 254 can move to the first direction using a variety of technologies and methods. In a non-limiting example, the engagement member distal end 254 is biased in the first direction so that the engagement member distal end 254 moves to the first direction once the retractable catheter sheath 264 is at least partially withdrawn toward the elongate member proximal end 208. This can be accomplished by forming a predefined bend 259 at the engagement member distal end 254. The predefined bend 259 permits the engagement member distal end 254 to move to the first direction when the retractable catheter sheath 264 is at least partially withdrawn toward the elongate member proximal end 208. This may also be accomplished by manufacturing the engagement member distal end 254 from viscoelastic and/or elastic materials. These materials enable the engagement member distal end 254 to return to its original shape (the first direction) after a force is removed (e.g., the retractable catheter sheath 264 no longer abutting the engagement portion 258 after being at least partially withdrawn). Other technologies and methods for biasing the engagement member distal end 254 in the first direction can also be employed, as desired.

Figure 9:
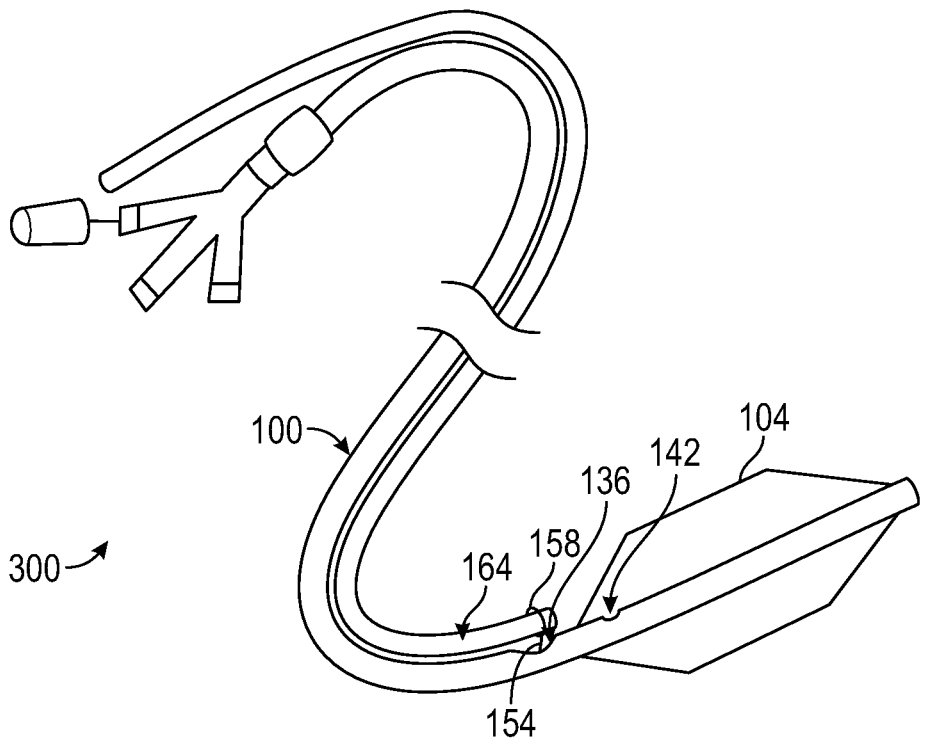
FIG. 9 is a top view, partially broken away, of an example catheter system. The secondary instrument is engaged with an engagement member of the catheter.

FIG. 9 illustrates an example catheter system 300. The catheter system 300 includes the first example catheter 100, described above and illustrated in FIGS. 1 through 5, secondary instrument 160, which is an endoscope in the illustrated example. A catheter system can include a catheter according to any embodiment and can include any suitable secondary instrument. Also, a catheter system can include a secondary instrument joined with the engagement member of the catheter, such as in the example illustrated in FIG. 9, or the secondary instrument can be free of the engagement member until later joined with the engagement member by a user of the catheter system.

Figure 10:
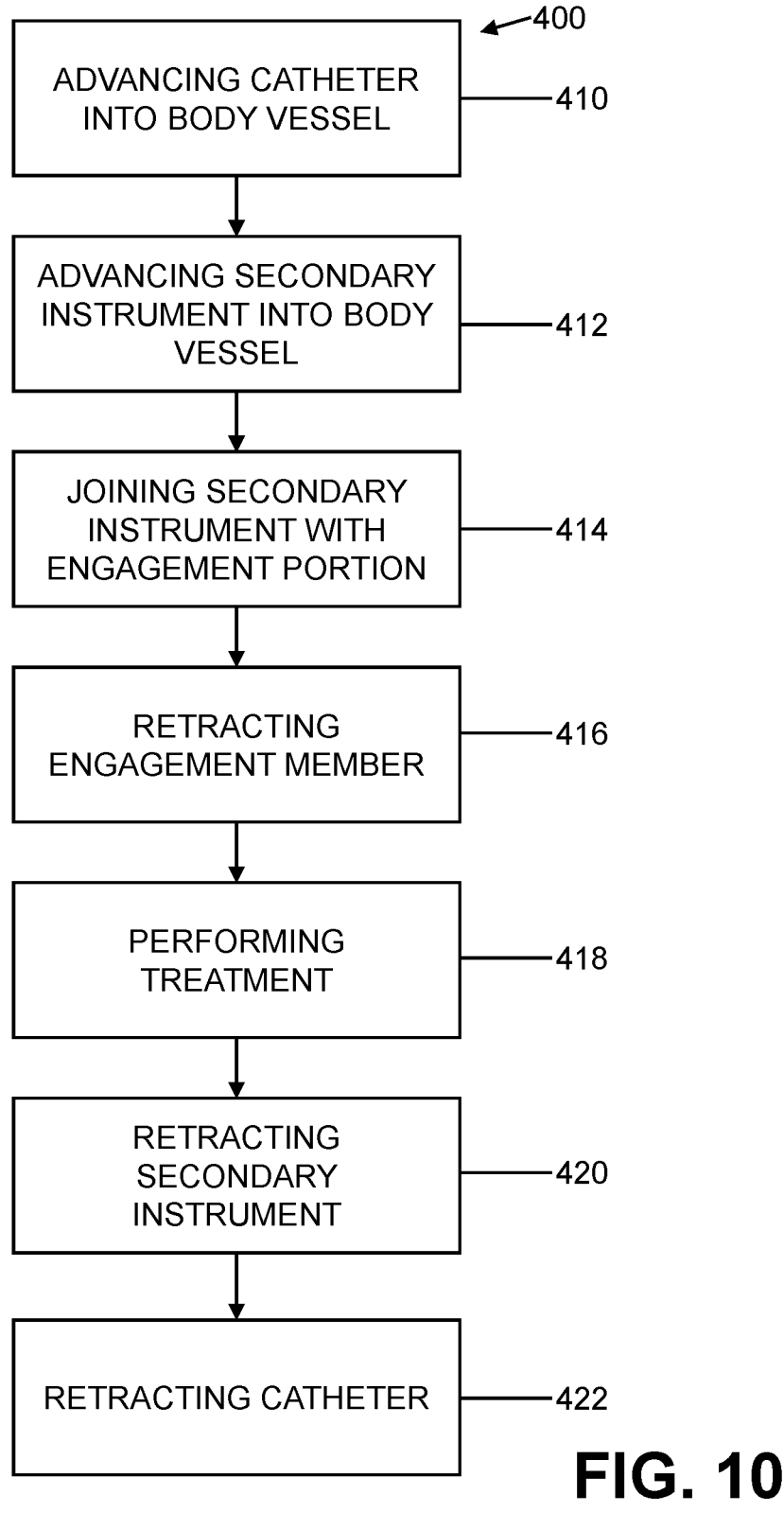
FIG. 10 is a flowchart illustration of an example method of treatment.

FIG. 10 illustrates an example method of treatment 400. An initial step 410 comprises advancing a catheter into a body vessel of a patient. This can be accomplished by advancing a catheter according to an embodiment, such as catheter 100 described above and illustrated in FIGS. 1 through 5, along a guidewire that has been previously placed within the body vessel. Another step 412 comprises advancing a secondary instrument through a body vessel to the engagement portion of the catheter. Another step 414 comprises joining the secondary instrument with the engagement portion to engage the secondary instrument with the catheter. Another step 416 comprises retracting the engagement member within the second lumen of the catheter, effectively drawing the engagement portion toward the side opening of the elongate member of the catheter and pulling the secondary instrument toward the side opening of the elongate member. This allows the practitioner to maintain the secondary instrument in close proximity to the balloon. Another step 418 comprises performing a treatment within the body vessel using the catheter. Another step 420 comprises retracting the secondary instrument through the body vessel to disengage the secondary instrument from the catheter. Another step 422 comprises retracting the catheter through the body vessel. Additional optional steps can include actions related to the nature of the secondary instrument. For example, if the secondary instrument is an endoscope, a step of visualizing the balloon using the secondary instrument while the secondary instrument is joined to the catheter can be included.

Step 412 can be performed by advancing the secondary instrument through the same body vessel within which the catheter was advanced in step 410, or by advancing the secondary instrument through a body vessel that is in communication with the body vessel within which the catheter was advanced in step 410 until the secondary instrument is positioned alongside the catheter within the same body vessel. For example, in step 410, the catheter can be advanced through a nostril of the patient and into the esophagus and, in step 412, the secondary instrument can be advanced through the other nostril of the patient and into the esophagus until the secondary instrument is positioned alongside the catheter within the esophagus of the patient.

In examples where the engagement portion is a loop, such as engagement portion 158 in catheter 100 described above and illustrated in FIGS. 1 through 5, step 414 can be performed by advancing the distal end of the secondary instrument at least partially through the loop.

Step 418 can be performed using techniques suitable and appropriate based on the structure and capabilities of the catheter used in the method 400. For example, in methods using catheter 100, described above and illustrated in FIGS. 1 through 5, the step 412 can comprise inflating the balloon to dilate tissue surrounding the balloon, and subsequently deflating the balloon. Other non-limiting examples of techniques that can be used to perform this step, dependent on the structure and capabilities of the catheter used in the method, include deploying a stent from the catheter, such as a balloon expandable stent or a self-expandable stent, deploying another type of implantable device from the catheter, such as a filter, a valve, a stent graft, or the like, and delivering a treatment agent, such as a medicament, to a point of treatment in the body vessel.

One or more additional optional steps can be included. For example, an optional step of manipulating the proximal end of the engagement member to releasably secure the engagement member in a desired position, such as a desired extension distance of the engagement member distal end out of the side opening of the elongate member, can be included. For example, if included, this step can be performed after step 416, after step 418, or after both of steps 416 and step 418 by manipulating the proximal end of the engagement member to releasably lock tension of the engagement portion of the engagement member distal end around the engaged secondary instrument.

Figure 11:
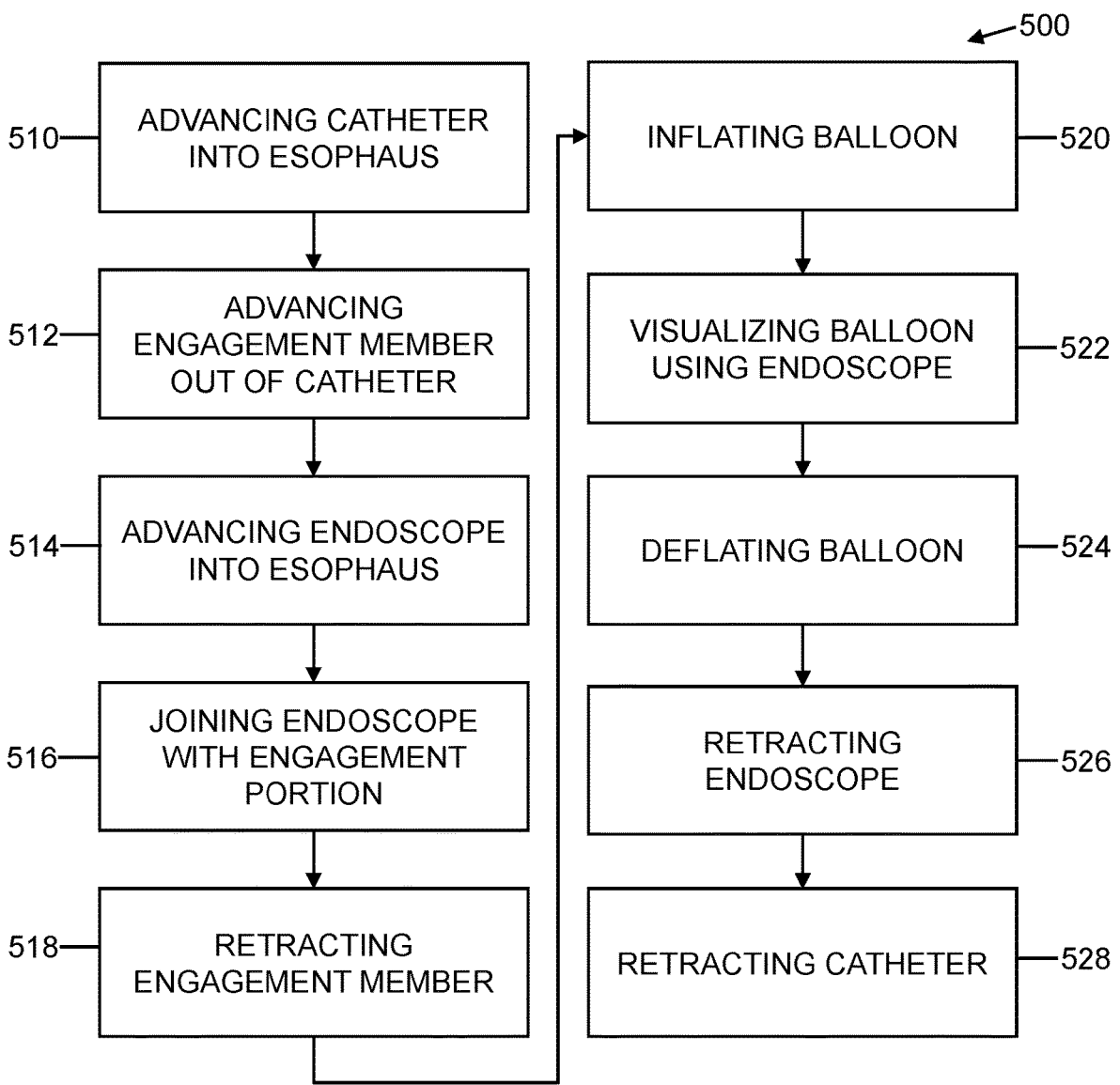
FIG. 11 is a flowchart illustration of another example method of treatment.

FIG. 11 illustrates an example method 500 of performing transnasal esophageal dilation. An initial step 510 comprises advancing a catheter through a nostril and into the esophagus of a patient. This can be accomplished by advancing a catheter according to an embodiment, such as catheter 100 described above and illustrated in FIGS. 1 through 5, along a guidewire that has been previously placed within the body vessel. Another step 512 comprises advancing the engagement member of the catheter within the second lumen of the catheter to extend the engagement portion of the catheter out of the side opening of the catheter. Another step 514 comprises advancing an endoscope through a nostril and into the esophagus of the patient to the engagement portion of the catheter. The nostril can be the same nostril through which the catheter was advanced in step 510, or the other nostril of the patient. Another step 516 comprises joining the distal end of the endoscope with the engagement portion of the catheter to engage the endoscope with the catheter. Another step 518 comprises retracting the engagement member within the second lumen of the catheter, effectively drawing the engagement portion toward the side opening of the elongate member of the catheter and pulling the endoscope toward the side opening of the elongate member. This allows the practitioner to maintain the secondary instrument in close proximity to the balloon. Another step 520 comprises inflating the balloon of the catheter to dilate tissue of the esophagus surrounding the balloon. Another step 522 comprises visualizing the balloon using the endoscope while the secondary instrument is joined to the catheter can be included. Another step 524 comprises deflating the balloon of the catheter. Another step 526 comprises retracting the endoscope through the nostril to disengage the endoscope from the catheter. Another step 528 comprises retracting the catheter through the nostril.

One or more additional optional steps can be included. For example, an optional step of manipulating the proximal end of the engagement member to releasably secure the engagement member in a desired position, such as a desired extension distance of the engagement member distal end out of the side opening of the elongate member, can be included. For example, if included, this step can be performed after step 516, after step 518, or after both of steps 516 and step 518 by manipulating the proximal end of the engagement member to releasably lock tension of the engagement portion of the engagement member distal end around the engaged endoscope.

Advantageously, each of the catheters 100, 200, the system 300, and the methods of treatment 500, 600 facilitate aligning the secondary instrument 160 in a side-by-side configuration with the elongate member 102, 202. The secondary instrument 160 can be aligned so that the end portion of the secondary instrument 160 is adjacent to the balloon proximal portion 146, 246, while also being between the elongate member proximal end 108, 208 and the balloon proximal portion 146, 246. This configuration also militates against the secondary instrument 160 from slipping out of alignment by contacting the balloon 104, 204.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply to describe and illustrate examples of the invention and are not intended to limit the scope of the invention or its protection, which is to be given the full breadth of the appended claims and any and all equivalents thereof.

What is claimed is:

1. A catheter, comprising:

an elongate member defining an elongate member proximal end, an elongate member distal end, an outer surface, and a main body, the outer surface defining a side opening at a position between the elongate member proximal end and the elongate member distal end, the main body defining a first lumen, a second lumen, and a third lumen, the first lumen extending from the elongate member proximal end to the elongate member distal end, the second lumen extending from the elongate member proximal end to the side opening, the third lumen extending from the elongate member proximal end toward the elongate member distal end;

a balloon disposed on the elongate member between the side opening and the elongate member distal end, the balloon having a balloon wall that defines a balloon cavity in fluid communication with the third lumen;

an engagement member disposed in the second lumen, the engagement member defining an engagement member proximal end and an engagement member distal end, the engagement member proximal end extending axially beyond the elongate member proximal end, the engagement member distal end extending radially beyond the side opening toward the elongate member proximal end and biased in a radially outward direction relative to the outer surface of the elongate member, the engagement member distal end having an engagement portion; and a retractable catheter sheath disposed over the elongate member, the balloon, and the engagement member distal end, the retractable catheter sheath abutting the engagement portion.

2. The catheter of claim 1, wherein the balloon defines a balloon distal portion and a balloon proximal portion, the balloon distal portion is disposed between the balloon proximal portion and the elongate member distal end, and the balloon proximal portion is disposed between the side opening and the balloon distal portion.

3. The catheter of claim 2, wherein the position of the side opening is between the elongate member proximal end and the balloon proximal portion.

4. The catheter of claim 1, wherein the engagement member distal end is biased in the first direction.

5. The catheter of claim 1, wherein the engagement member distal end includes a predefined bend in the first direction.

6. The catheter of claim 1, wherein the engagement portion is a loop.

7. A method of performing a medical procedure, comprising:

advancing the catheter of claim 1 into a body vessel of a patient;

advancing a secondary instrument through the body vessel to the engagement portion of the catheter;

joining the secondary instrument with the engagement portion to engage the secondary instrument with the engaging member;

retracting the engagement member within the second lumen of the catheter to move the engagement portion toward the side opening of the elongate member of the catheter and to move the secondary instrument toward the side opening of the elongate member;

performing a treatment within the body vessel using the catheter;

retracting the secondary instrument through the body vessel to disengage the secondary instrument from the engagement member; and retracting the catheter through the body vessel.

8. The method of claim 7, wherein performing the treatment includes inflating the balloon to an expanded configuration to dilate tissue surrounding the balloon and subsequently deflating the balloon to an unexpanded configuration.

* * * * *